(12) United States Patent
Jonckers et al.

(10) Patent No.: US 8,664,391 B2
(45) Date of Patent: Mar. 4, 2014

(54) AMIDE COMPOUNDS AS BOOSTERS OF ANTIVIRALS

(75) Inventors: Tim Hugo Maria Jonckers, Edegem (BE); Wim Bert Griet Schepens, Mechelen (BE); Geerwin Yvonne Paul Haché, Kapellen (BE); Beate Sabine Hallenberger, Bromskirchen (DE); Jennifer Chiyomi Sasaki, Raritan, NJ (US); Judith Eva Baumeister, Mechelen (BE); Gerben Albert Van 'T Klooster, Breda (NL)

(73) Assignee: Janssen R&D Ireland Ltd, Little Island Co, Cork (IE)

( * ) Notice: Subject to any disclaimer, the term of this patent is extended or adjusted under 35 U.S.C. 154(b) by 130 days.

(21) Appl. No.: 13/122,817

(22) PCT Filed: Oct. 7, 2009

(86) PCT No.: PCT/EP2009/062996
§ 371 (c)(1),
(2), (4) Date: Apr. 6, 2011

(87) PCT Pub. No.: WO2010/040762
PCT Pub. Date: Apr. 15, 2010

(65) Prior Publication Data
US 2011/0195969 A1    Aug. 11, 2011

(30) Foreign Application Priority Data

Oct. 7, 2008 (EP) .................................. 08166004

(51) Int. Cl.
*C07D 241/36* (2006.01)
(52) U.S. Cl.
USPC ............................. 544/355; 548/202; 560/41
(58) Field of Classification Search
USPC ............................. 544/355; 548/202; 560/41
See application file for complete search history.

(56) References Cited

U.S. PATENT DOCUMENTS 6,037,157 A    3/2000    Norbeck et al.

FOREIGN PATENT DOCUMENTS

| WO | WO 03/049746 A2 | 6/2003 |
|---|---|---|
| WO | WO 2005/030194 A1 | 4/2005 |
| WO | WO 2006/108879 A2 | 10/2006 |
| WO | WO 2008/027932 A2 | 3/2008 |
| WO | WO 2009/071650 A2 | 6/2009 |

OTHER PUBLICATIONS

Kempf, D.J., et al. "Pharmacokinetic Enhancement of Inhibitors of the Human Immunodeficiency Virus Protease by Coadministration with Ritonavir", Antimicrobial Agents and Chemotherapy, (1997), vol. 41, No. 3, pp. 654-660.
Goodman and Gilman, "The Pharmacological Basis of therapeutics", Eighth Edition, Chapter 11, (1990) "Biotransformmation of Drugs", pp. 13-15.
Gorrod, J.W., "The Metabolism of N-Ethyl-N-methylaniline by Rabbit Liver Microsomes: The Measurement of Metabolites by Gas-liquid Chromatography", Xenobiotica, (1975), vol. 5, No. 8, pp. 453-463.
International Search report for Application No. PCT/EP2009/062996 mailed Dec. 14, 2009.

*Primary Examiner* — Douglas M Willis
(74) *Attorney, Agent, or Firm* — Michael J. Atkins

(57) ABSTRACT

The present invention relates to compounds of formula (I) that have CYP450 inhibiting properties and are useful as boosting agents when used with HIV treatments. These compounds are represented by formula

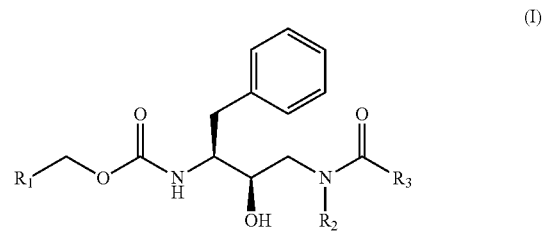

(I)

including the salts and stereoisomeric forms thereof, wherein $R_1$ is 5-thiazolyl or 3-pyridinyl; $R_2$ is iso-butyl, 2,2-dimethylpropyl; 2-hydroxy-2-methyl-propyl or cyclohexylmethyl; $R_3$ is phenyl optionally substituted with one or more halogens, trifluoromethyl, $C_{1-6}$-alkyl or $C_{1-6}$-alkoxy wherein optionally two of said alkoxy groups are be linked to each other to form a 5 or 6-membered ring; heteroaryl; $C_{3-7}$-cycloalkyl optionally substituted with one or more halogens; $C_{1-6}$alkyl optionally substituted with heteroaryl; —O—$CH_2$— (heteroaryl). As boosting agents they are able to increase at least one of the pharmacokinetic variables of certain drugs when co-administered, or improve the bioavailability of certain drugs. Methods for the preparation of the compounds of the invention and pharmaceutical compositions comprising these compounds are also provided.

1 Claim, No Drawings

AMIDE COMPOUNDS AS BOOSTERS OF ANTIVIRALS

CROSS REFERENCE TO RELATED APPLICATIONS

This application is a national stage of PCT Application No. PCT/EP2009/062996, filed Oct. 7, 2009, which claims priority from European Patent Application No. 08166004.5, filed Oct. 7, 2008, all of which are hereby incorporated by reference in their entirety.

The present invention relates to compounds that have CYP450 inhibiting properties and are therefore useful as boosters of certain drugs, i.e. they are able to increase at least one of the pharmacokinetic variables of certain drugs when co-administered. The invention further provides the use of said compounds as improvers of the bioavailability of certain drugs. Methods for the preparation of the compounds of the invention and pharmaceutical compositions comprising these compounds are also provided.

Many drugs, including some HIV protease inhibitors (PIs) and non-nucleoside reverse transcriptase inhibitors (NNRTIs), are metabolized by the cytochrome P450 system. The cytochrome P450 system is a group of enzymes found in the liver and the gut, which have a number of functions in the human body. The activity of cytochrome P450 differs between individuals and between populations. Small genetic variations can affect how many particular enzymes are expressed, and thus how quickly the drug is metabolized.

Cytochrome P450 enzymes which derive from a particular gene are called isoforms. Based on the similarity of their chemical make-up, isoforms are divided into families and subfamilies. Enzyme variants are described through a numbering and lettering system, which reflects their chemical and genetic structure.

Cytochrome P450, subfamily IIIA (niphedipine oxidase), polypeptide 4, also referred to as CYP3A4, is one particular metabolic pathway used for breakdown and clearance of medications and other substances.

Metabolization of certain drugs by the cytochrome P450 system frequently results in said drugs having unfavourable pharmacokinetics and the need for more frequent and higher doses than are most desirable. Administration of such drugs with an agent that inhibits metabolism by the cytochrome P450 system may improve the pharmacokinetics of the drug. In this respect, methods for improving the pharmacokinetics of certain drugs have been published, see, e.g., U.S. Pat. No. 6,037,157; D. E. Kempf et al. Antimicrob. Agents Chemother., 41, pp. 654-660 (1997).

In WO03/049746 there is disclosed a method for improving the pharmacokinetics of hexahydrofuro[2,3-b]furanyl containing HIV protease inhibitors comprising administering to a human in need thereof a combination of a therapeutically effective amount of a hexahydrofuro[2,3-b]furanyl containing HIV protease inhibitor, and a therapeutically effective amount of a cytochrome P450 inhibitor.

Most HIV protease inhibitors in clinical therapy are now paired with ritonavir to improve exposure and thereby enhancing clinical efficacy. This type of applied drug-drug interaction is referred to as "boosting". Boosting also supports simplified treatment regimens for current PIs by reduction of pill burden and frequency of daily intakes.

Unfortunately, ritonavir enhancement of PI regimens, even at low doses, is not without risk. Ritonavir is itself an HIV protease inhibitor. Resistance to ritonavir is associated with the selection of one or more of several resistance mutations. Resistance mutations selected by ritonavir frequently confer or contribute to resistance against other protease inhibitors. Different mutations are associated with cross-resistance to different drugs. For example, M46I is associated with cross-resistance to indinavir, nelfinavir, and fosamprenavir (but not to saquinavir); V82A,F,T,S alone is associated with cross-resistance to indinavir, but in combination with other mutations also confers resistance to nelfinavir, fosamprenavir, and saquinavir; and I84V contributes to resistance against all available protease inhibitors. While no single one of these mutations is associated with full resistance to lopinavir, each contributes partial resistance, and the presence of several mutations together can confer resistance. Response to indinavir is unlikely in the setting of resistance to ritonavir.

As such, there is a high medical need for alternatives to ritonavir as boosting agent in an effective and safe anti-HIV treatment. There is also a high medical for alternatives to ritonavir as boosting agent in an effective and safe anti-HIV treatment wherein the possibility of resistance development due to the boosting agent is excluded.

In accordance with the present invention it has now been found that the following compounds of formula (I) have CYP450 inhibiting properties and are useful as boosting agents. These compounds are represented by formula

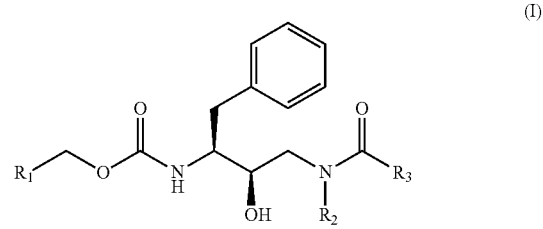

(I)

the salts and stereoisomeric forms thereof, wherein
$R_1$ is 5-thiazolyl or 3-pyridinyl;
$R_2$ is iso-butyl, 2,2-dimethylpropyl; 2-hydroxy-2-methylpropyl or cyclohexyl-methyl;
$R_3$ is phenyl optionally substituted with one or more halogens, trifluoromethyl, $C_{1-6}$-alkyl or $C_{1-6}$-alkoxy wherein optionally two of said alkoxy groups are be linked to each other to form a 5 or 6-membered ring; heteroaryl; $C_{3-7}$-cycloalkyl optionally substituted with one or more halogens; $C_{1-6}$alkyl optionally substituted with heteroaryl; —O—$CH_2$— (heteroaryl).

Preferred compounds are those compounds wherein $R_1$ is 5-thiazolyl, $R_2$ is iso-butyl and $R_3$ is quinoxalyl.

Most preferred is the compound having the formula (II)

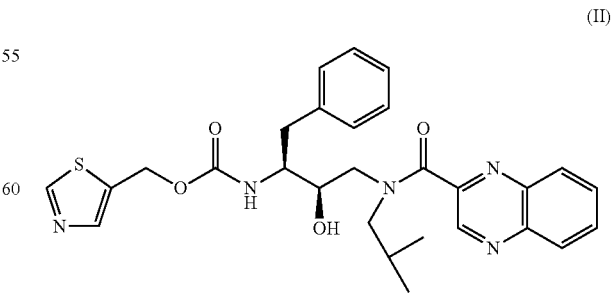

(II)

the salts and stereoisomeric forms thereof, said compound having the chemical name 1S-2R-{1-Benzyl-2-hydroxy-3-

[isobutyl-(quinoxaline-2-carbonyl)-amino]-propyl}-carbamic acid thiazol-5-ylmethyl ester.

The above mentioned compounds have been found to confer minimal or no resistance against HIV and are therefore useful alternatives for ritonavir (RTV) as boosters of HIV inhibitors.

It has also been found that the above compounds are useful as boosting agents of other viral inhibitors such as for instance HCV and/or RSV inhibitors. The combination of said compounds and other drugs, such as HIV, HCV or RSV inhibitors is beneficial in that it permits the provision of a therapy to infected patients which is safe, is effective, and allows a lower therapeutically effective dose of antivirals, compared to when such antivirals would be administered alone. A lower dose is always desirable in terms of toxicity and pill burden, thereby diminishing the incidence of adverse effects and increasing treatment compliance, respectively. The combination of the compounds of formula (I) and (II) and HIV inhibitors, or other viral inhibitors, provides a synergistic effect on these antivirals upon administration of said combination to a patient in need thereof.

As used in the foregoing and hereinafter, the following definitions apply unless otherwise noted.

Whenever the term "substituted" is used in defining the compounds of the invention, it is meant to indicate that one or more hydrogens on the atoms mentioned or comprised in the expression using "substituted" is replaced with a selection from the indicated group, provided that the said atoms' normal valency is not exceeded, and that the substitution results in a chemically stable compound, i.e. a compound that maintains its structural and molecular identity in a useful degree of purity through a convenient amount of time. The convenient amount of time will depend on the field of application.

The term halo(gen) is generic to fluoro, chloro, bromo and iodo.

As used herein "$C_{1-4}$ alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl;
"$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl especially isobutyl.

$C_{3-7}$cycloalkyl is generic to cyclopropyl, cyclobutyl, cyclopentyl, cyclohexyl and cycloheptyl.

"Heteroaryl" is art-recognized and refers to a monocyclic or bicyclic ring system containing one or two five (5)- or six (6)-member (fused) aromatic rings; said ring system contains at least one hetero atom selected from nitrogen, oxygen or sulfur and said hetero atoms are optionally substituted with $C_{1-6}$ alkyl.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl.

Whenever used hereinafter, the term "compounds of formula (I) for instance", "the present compounds", "the compounds of the invention" or similar terms, it is meant to include the compounds of formula (I) and any subgroup thereof, the compounds as depicted in the Tables and Examples below, and the prodrugs, stereochemically isomeric forms, racemic mixtures, esters, addition salts, solvates, quaternary amines, N-oxides, metal complexes, and metabolites of any of the compounds above. One embodiment comprises the compounds of formula (I), or any subgroup thereof specified herein, as well as the N-oxides, salts, as well as possible stereoisomeric forms thereof.

Whenever used hereinafter, the term "HIV antiviral(s)" and "HIV inhibitor(s)" are interchangeable and have in the context of the current description the same meaning.

The compounds of formula (I) may encompass centers of chirality in their substituents and therefore exist as stereochemically isomeric forms. The terms "stereochemically isomeric forms", "stereoisomeric forms", and equivalent terminology as used herein defines all the possible compounds made up of the same atoms bonded by the same sequence of bonds but having different three-dimensional structures which are not interchangeable, which the compounds of formula (I) may possess.

With reference to the instances where (R) or (S), or alternatively indicated by an asterisk (*), is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of the invention can be obtained separately by conventional methods. Appropriate physical separation methods that may advantageously be employed are, for example, selective crystallization and chromatography, e.g. column chromatography.

For certain compounds of the invention, their prodrugs, N-oxides, salts, solvates, quaternary amines, or metal complexes, and the intermediates used in the preparation thereof, the absolute stereochemical configuration is not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxy-methyl esters for example methoxymethyl, $C_{1-6}$alkanoyloxymethyl esters for example pivaloyloxymethyl, phthalidyl esters, $C_{3-8}$cycloalkoxycarbonyloxy-$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyl-oxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylamino-acetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methane-sulfonic, ethanesulfonic, benzenesulfonic, p-toluenesulfonic, cyclamic, salicylic, p-aminosalicylic, palmoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvate" is used herein to describe a molecular complex comprising i) the compounds of the invention as well as the salts thereof, and ii) one or more pharmaceutically acceptable solvent molecules, for example, ethanol, isopropanol, 1-methoxy-2-propanol, methanol, acetone, dichloromethane, ethylacetate, anisol, tetrahydrofurane, or mesylate. The term "hydrate" is employed when said solvent is water.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluene-sulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

The compounds of formula (I) have two asymmetric centers as depicted by the asterisk below:

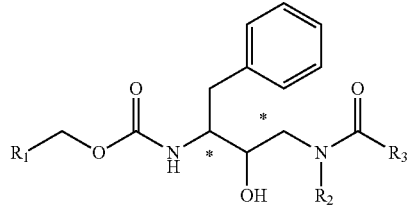
(I)

Preferably the compounds of formula (I) have the stereochemistry as indicated in the structure of formula (I-a) below:

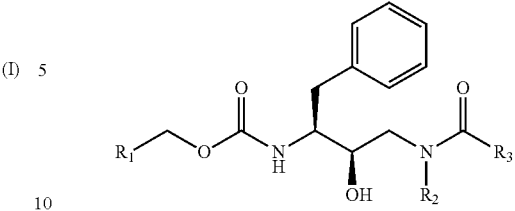
(I-a)

The compounds of formula (I) according to the present invention can be selected from any one of the following compounds of Table 1. Besides the substitution pattern (indicated by R, $R_1$, $R_2$) the LC-MS data (m/z (M+1) & retention time ($R_t$) is reported. The results and examples given are presented to exemplify the invention and are not to be construed as limiting the scope of the invention.

(I)

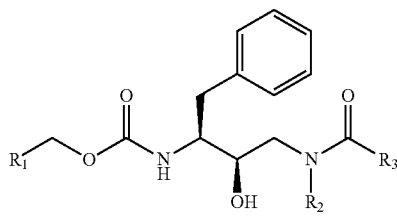

| Comp. No. | $R_1$ | $R_2$ | $R_3$ | m/z (M + 1) | Rt(min) |
|---|---|---|---|---|---|
| C1 | 5-thiazolyl | isobutyl | benzodioxole | 526 | 2.19 |
| C2 | 5-thiazolyl | isobutyl | benzofuran | 522 | 2.29 |
| C3 | 5-thiazolyl | isobutyl | 4-isopropylphenyl | 496 | 2.36 |
| C4 | 5-thiazolyl | isobutyl | 4-(trifluoromethyl)phenyl | 550 | 2.49 |
| C5 | 5-thiazolyl | isobutyl | 4-methoxyphenyl | 512 | 2.23 |
| C6 | 5-thiazolyl | isobutyl | 4-fluorophenyl | 500 | 2.26 |
| C7 | 5-thiazolyl | isobutyl | 3-methoxyphenyl | 512 | 2.25 |

-continued

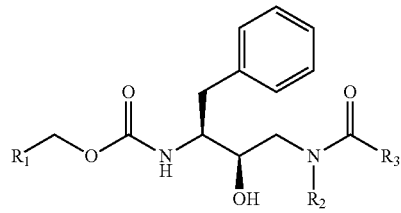
(I)

| Comp. No. | R₁ | R₂ | R₃ | m/z (M+1) | Rt(min) |
|---|---|---|---|---|---|
| C8 | 5-thiazolyl | isobutyl | 4-pyridyl | 483 | 3.84 |
| C9 | 5-thiazolyl | isobutyl | 2-pyridyl | 483 | 2.02 |
| C10 | 5-thiazolyl | isobutyl | 3-methylphenyl | 496 | 2.36 |
| C11 | 5-thiazolyl | isobutyl | 3-trifluoromethylphenyl | 550 | 2.48 |
| C12 | 5-thiazolyl | isobutyl | 2-quinoxalinyl | 534 | 2.32 |
| C13 | 5-thiazolyl | isobutyl | 3-pyridyl | 483 | 1.88 |
| C14 | 5-thiazolyl | isobutyl | 2-pyrrolyl | 471 | 2.13 |
| C15 | 5-thiazolyl | isobutyl | 3-chlorophenyl | 516 | 2.49 |
| C16 | 5-thiazolyl | isobutyl | 4-chlorophenyl | 516 | 2.41 |
| C17 | 5-thiazolyl | isobutyl | 3-bromophenyl | 560 | 4.92 |
| C18 | 5-thiazolyl | isobutyl | 4-bromophenyl | 560 | 2.45 |

-continued

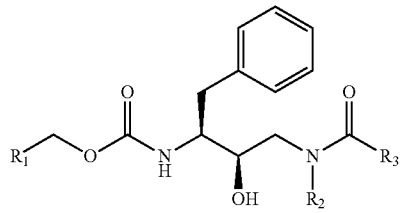
(I)

| Comp. No. | R₁ | R₂ | R₃ | m/z (M + 1) | Rt(min) |
|---|---|---|---|---|---|
| C19 | 5-thiazolyl | isobutyl | 3-fluorophenyl | 500 | 2.27 |
| C20 | 3-pyridinyl | isobutyl | 4-pyridinyl | 477 | 1.79 |
| C21 | 5-thiazolyl | isobutyl | 2-furyl | 472 | 2.12 |
| C22 | 5-thiazolyl | 2,2-dimethylpropyl | 4-pyridinyl | 497 | 4.05 |
| C23 | 5-thiazolyl | isobutyl | 4,4-difluorocyclohexyl | 524 | 2.36 |
| C24 | 5-thiazolyl | isobutyl | 2-(5-thiazolyl)ethyl | 517 | 3.88 |
| C25 | 5-thiazolyl | isobutyl | (5-thiazolyl)methoxy | 519 | 2.13 |
| C26 | 5-thiazolyl | 2-hydroxy-2-methyl-propyl | 4-pyridinyl | 499 | 1.47 |
| C27 | 5-thiazolyl | cyclohexylmethyl | 4-pyridinyl | 523 | 2.17 |

Preferred compound is compound C12.

In a preferred embodiment of the present invention there is provided a combination comprising (a) a compound of formula (I), a salt or a stereoisomeric form thereof; and (b) an HIV antiviral, or a pharmaceutically acceptable salt thereof; wherein the compound of formula (I) is C12.

In a preferred embodiment of the present invention there is provided a combination comprising (a) a compound of formula (I), a salt or a stereoisomeric form thereof; and (b) an HIV antiviral, or a pharmaceutically acceptable salt thereof; wherein the compound of formula (I) is C12 and wherein the HIV antiviral is selected from for instance: nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), apricitabine (AVX-754), elvucitabine (ACH-126,443), phosphazide, KP-1461, MIV-210, racivir (PSI-5004), and the like; or non-nucleoside reverse transcriptase inhibitors (NNRTIs) such as delavirdine (DLV), efavirenz (EFV), nevirapine (NVP), capravirine (CPV), calanolide A, dapivirine (TMC120), etravirine (TMC125), rilpivirine (TMC278), alovudine (MIV-310), UC-781, and the like; or nucleotide reverse transcriptase inhibitors (NtRTIs), e.g. tenofovir and tenofovir disoproxil fumarate (TDF), and the like; or inhibitors of trans-activating proteins, such as TAT-inhibitors, e.g. RO-5-3335, BI-201; REV inhibitors; or protease inhibitors e.g. ritonavir (RTV), saquinavir (SQV), lopinavir (ABT-378 or LPV), indinavir (IDV), amprenavir (VX-478), TMC-126, nelfinavir (AG-1343), atazanavir (BMS-232632), darunavir (TMC-114) now marketed as Prezista™, SPI-256, fosamprenavir (GW433908 or VX-175), P-1946, MK-8122 (PPL-100), tipranavir (PNU-140690), or a protease inhibitor with the chemical name (1-benzyl-3-{[2-(1-cyclopentyl-piperidin-4-ylamino)-benzothiazole-6-sulfonyl]-isobutyl-amino}-2-hydroxy-propyl)-carbamic acid hexahydro-furo[2,3-b]furan-3-yl ester, and the like; or viral integrase inhibitors e.g. raltegravir (MK-518), elvitegravir (GS-9137; JTK-303), BMS-538,158, and the like; or entry inhibitors which comprise fusion inhibitors (e.g. T-20 or enfuvirtide, T-1249), attachment inhibitors and co-receptor inhibitors; the latter comprise the CCR5 antagonists and CXR4 antagonists (e.g. AMD-3100); examples of entry inhibitors are PRO-140, PRO-542, TBR-220 (TAK-220), TBR-652 (TAK-652), vicriviroc (SCH-417,690), TNX-355, maraviroc (UK-427, 857), BMS-488,043, BMS-806; a maturation inhibitor for example is bevirimat (PA-457); ribonucleotide reductase inhibitors (cellular inhibitors), e.g. hydroxyurea and the like; or combinations of any of the above.

Most preferred embodiment is a combination comprising (a) a compound C12, a salt or a stereoisomeric form thereof; and (b) an HIV antiviral selected from darunavir ([(1R,5S,6R)-2,8-dioxabicyclo[3.3.0]oct-6-yl]N-[(2S,3R)-4-[(4-amino-phenyl)sulfonyl-(2-methylpropyl)amino]-3-hydroxy-1-phenyl-butan-2-yl]-carbamate) or a compound with the chemical name (1-benzyl-3-{[2-(1-cyclopentyl-piperidin-4-ylamino)-benzothiazole-6-sulfonyl]-isobutyl-amino}-2-hydroxy-propyl)-carbamic acid hexahydro-furo[2,3-b]furan-3-yl ester.

In one embodiment of the present invention there is provided a process for preparing a combination as described herein, comprising the step of combining a compound of formula (I) or a pharmaceutically acceptable salt thereof, and an HIV antiviral, or a pharmaceutically acceptable salt thereof. An alternative embodiment of this invention provides a process wherein the combination comprises one or more additional agent as described herein.

The combinations of the present invention may be used as medicaments. Said use as a medicine or method of treatment comprises the systemic administration to HIV-infected subjects of an amount effective to combat the conditions associated with HIV. Consequently, the combinations of the present invention can be used in the manufacture of a medicament useful for treating, preventing or combating infection or disease associated with HIV infection in a mammal.

In one embodiment of the present invention there is provided a pharmaceutical composition comprising a combination according to any one of the embodiments described herein and a pharmaceutically acceptable excipient. In particular, the present invention provides a pharmaceutical composition comprising (a) a therapeutically effective amount of a compound of formula (I) or a pharmaceutically acceptable salt thereof, (b) a therapeutically effective amount of an HIV antiviral, or a pharmaceutically acceptable salt thereof, and (c) a pharmaceutically acceptable excipient. Optionally, the pharmaceutical composition further comprises an additional agent selected from an HIV antiviral.

As used herein, the term "composition" is intended to encompass a product comprising the specified ingredients, as well as any product which results, directly or indirectly, from the combination of the specified ingredients.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) an HIV antiviral, would be the amount of the compound of formula (I) and the amount of the HIV antiviral that when taken together have a combined effect that is therapeutically effective.

The pharmaceutical composition can be prepared in a manner known per se to one of skill in the art. For this purpose, at least one of a compound of formula (I) or any subgroup thereof, and an HIV antiviral, together with one or more solid or liquid pharmaceutical excipients and, if desired, in combination with other pharmaceutical active compounds, are brought into a suitable administration form or dosage form which can then be used as a pharmaceutical in human medicine or veterinary medicine.

In one embodiment the combinations of the present invention may also be formulated as a combined preparation for simultaneous, separate or sequential use in HIV therapy, as applicable. In such a case, the compound of general formula (I) or any subgroup thereof, is formulated in a pharmaceutical composition containing other pharmaceutically acceptable excipients, and the appropriate HIV antiviral is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering" is to be interpreted accordingly. In a preferred embodiment, the separate dosage forms are administered about simultaneously.

The compositions or products comprising a combination of the present invention, whether co-formulated in a single formulation or formulated for simultaneous, separate or sequential use, may be administered orally (including suspensions, capsules, tablets, sachets, solutions, suspensions, emulsions), sublingually, parenterally (including subcutaneous injections, intravenous, intramuscular, intradermal injection or infusion techniques), topically, rectally (including suppositories), vaginally, via an implanted reservoir, in dosage unit formulations containing conventional non-toxic pharmaceutically acceptable carriers, adjuvants and vehicles.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

The oral administration of a combination of the present invention is suitably accomplished by uniformly and intimately blending together a suitable amount of each component in the form of a powder, optionally also including a finely divided solid carrier, and encapsulating the blend in, for example, a hard gelatin capsule. The solid carrier can include one or more substances which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinyl-pyrrolidine, low melting waxes and ion exchange resins.

Oral administration of a combination of the present invention can also be accomplished by preparing capsules or tablets containing the desired amount of the compound of formula (I) only, optionally blended with a solid carrier as described above, and capsules containing the desired amount of the HIV antiviral only. Compressed tablets containing the compound of formula (I) can be prepared by uniformly and intimately mixing the active ingredient with a solid carrier such as described above to provide a mixture having the necessary compression properties, and then compacting the mixture in a suitable machine to the shape and size desired. Molded tablets maybe made by molding in a suitable machine, a mixture of powdered the compound of formula (I) moistened with an inert liquid diluents. Oral administration can also be accomplished by preparing compressed or molded tablets containing the compound of formula (I) as just described, the tablets of suitable size for insertion into standard capsules (e.g., hard gelatin capsules), and then inserting the tablets into capsules containing a suitable amount of HIV antiviral powder.

For subcutaneous or intravenous administration, the active components of the compositions, if desired with the substances customary therefore such as solubilizers, emulsifiers or further auxiliaries, are brought into solution, suspension, or emulsion. The components of the compositions can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract may be effected in a rectal suppository formulation (see below) or in a suitable enema formulation. Topically-transdermal patches may also be used.

For topical applications, the pharmaceutical compositions may be formulated in a suitable ointment containing the active components suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

When rectally administered in the form of suppositories, these formulations may be prepared by mixing the individual components of a composition according to the invention with a suitable non-irritating excipient, such as cocoa butter, synthetic glyceride esters or polyethylene glycols, which are solid at ordinary temperatures, but liquidify and/or dissolve in the rectal cavity to release the drug.

In another embodiment of the method of the invention, the administration may be performed with food (e.g., a high-fat meal) or without food. The term "with food" means the consumption of a meal either during or no more than about one hour before or after administration of a one or both components of the combination according to the invention.

In one embodiment, the combinations of the present invention contain an amount of a compound of formula (I), or a pharmaceutically acceptable salt thereof, which is sufficient to clinically improve the bioavailability of the HIV inhibitor or antiviral relative to the bioavailability when said HIV inhibitor or antiviral is administered alone.

In another embodiment, the combinations of the present invention contain an amount of a compound of formula (I), or a pharmaceutically acceptable salt thereof, which is sufficient to increase at least one of the pharmacokinetic variables of the HIV inhibitors selected from $t_{1/2}$, $C_{min}$, $C_{max}$, $C_{ss}$, AUC at for instance 12 hours, or AUC at for instance 24 hours, relative to said at least one pharmacokinetic variable when said HIV inhibitor is administered alone.

A further embodiment relates to a method for improving the bioavailability of an HIV inhibitor comprising administering to an individual in need of such improvement a combination as defined herein, comprising a therapeutically effective amount of each component of said combination.

In a further embodiment, the invention relates to the use of a compound of formula (I) or a pharmaceutically acceptable salt thereof, as an improver of at least one of the pharmacokinetic variables of an HIV inhibitor selected from $t_{1/2}$, $C_{min}$, $C_{max}$, $C_{ss}$, AUC at for instance 12 hours, or AUC at for instance 24 hours; with the proviso that said use is not practiced in the human or animal body.

The term "individual" as used herein refers to an animal, preferably a mammal, most preferably a human, who has been the object of treatment, observation or experiment.

Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$, represents the highest (maximum) concentration measured during the dosing interval. AUC is defined as the area under the plasma concentration-time curve for a defined period of time for instance at 12 hrs or 24 hrs.

The combinations of this invention can be administered to humans in dosage ranges specific for each component comprised in said combinations. The components comprised in said combinations can be administered together or separately. The HIV inhibitors, and the compound of formula (I) or a pharmaceutically acceptable salt or ester thereof, may have dosage levels of the order of 0.02 to 5.0 grams-per-day.

When the HIV inhibitor or antiviral and the compound of formula (I) are administered in combination, the weight ratio of the HIV inhibitor to the compound of formula (I) is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HIV inhibitor to compound of formula (I) ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HIV inhibitor is equal to or greater than that of the compound of formula (I), wherein the weight ratio of the HIV inhibitor to the compound of formula (I) is suitably in the range of from about 1:1 to about 15:1, typically from about 1:1 to about 10:1, and more typically from about 1:1 to about 8:1. Also useful are weight ratios of the HIV inhibitor to the compound of formula (I) ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

According to one embodiment, the HIV inhibitor and compound of formula (I) may be co-administered once or twice a day, once, twice, three, four, fives or six times a week, preferably orally, wherein the amount of the HIV inhibitor per dose is from about 10 to about 2500 mg, and the amount of the compound of formula (I) per dose is from 10 to about 2500 mg. In another embodiment, the amounts per dose for once or twice daily co-administration are from about 50 to about 1500 mg of the HIV inhibitor and from about 50 to about 1500 mg of the compound of formula (I). In still another embodiment, the amounts per dose for the daily or weekly co-administration are from about 100 to about 1000 mg of the HIV inhibitor and from about 100 to about 800 mg of the compound of formula (I). In yet another embodiment, the amounts per dose for the daily or weekly co-administration are from about 150 to about 800 mg of the HIV inhibitor and from about 100 to about 600 mg of the compound of formula (I). In yet another embodiment, the amounts per dose for the daily or weekly co-administration are from about 200 to about 600 mg of the HIV inhibitor and from about 100 to about 400 mg of the compound of formula (I). In yet another embodiment, the amounts per dose for the daily or weekly co-administration are from about 200 to about 600 mg of the HIV inhibitor and from about 20 to about 300 mg of the compound of formula (I). In yet another embodiment, the amounts per dose for the daily or weekly co-administration are from about 100 to about 400 mg of the HIV inhibitor and from about 40 to about 100 mg of the compound of formula (I).

Exemplary combinations of the HIV inhibitor (mg)/compound of formula (I) (mg) for twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the HIV inhibitor (mg)/compound of formula (I) (mg) for twice daily dosage include 1200/400, 800/400, 600/400, 400/200, 600/200, 600/100, 500/100, 400/50, 300/50, and 200/50.

It will be understood, however, that specific dose level and frequency of dosage for any particular patient may be varied and will depend upon a variety of factors including the activity of the specific compound employed, the metabolic stability and length of action of that compound; the age, body weight, general health, sex and diet of the patient; mode and time of administration, rate of excretion, drug combination, the severity of the particular condition, and the type of patient undergoing therapy.

In one embodiment of the present invention there is provided an article of manufacture comprising a composition effective to treat an HIV infection; and packaging material comprising a label which indicates that the composition can be used to treat infection by HIV; wherein the composition comprises the combination as described herein.

EXAMPLES

The results and examples given are presented to exemplify the invention and are not to be construed as limiting the scope of the invention.

The compounds according to the invention have been tested in various in vitro assays for which the results are listed in the Tables hereafter.

Assay 1 &2: Antiviral Activity/Toxicity

The compounds of the present invention were tested for antiviral activity in a cellular assay, which was performed according to the following procedure.

The human T-cell line MT4 is engineered with Green Fluorescent Protein (GFP) and an HIV-specific promoter, HIV-1 long terminal repeat (LTR). This cell line is designated MT4 LTR-EGFP, and can be used for the in vitro evaluation of anti-HIV activity of investigational compounds. In HIV-1 infected cells, the Tat protein is produced which upregulates the LTR promotor and finally leads to stimulation of the GFP reporter production, allowing measuring ongoing HIV-infection fluorometrically.

Analogously, MT4 cells are engineered with GFP and the constitutional cytomegalovirus (CMV) promotor. This cell line is designated MT4 CMV-EGFP, and can be used for the in vitro evaluation of cytotoxicity of investigational compounds. In this cell line, GFP levels are comparably to those of infected MT4 LTR-EGFP cells. Cytotoxic investigational compounds reduce GFP levels of mock-infected MT4 CMV-EGFP cells.

Effective concentration values such as 50% effective concentration ($EC_{50}$) can be determined and are usually expressed in μM. An $EC_{50}$ value is defined as the concentration of test compound that reduces the fluorescence of HIV-infected cells by 50%. The 50% cytotoxic concentration ($CC_{50}$ in μM) is defined as the concentration of test compound that reduces fluorescence of the mock-infected cells by 50%. The ratio of $CC_{50}$ to $EC_{50}$ is defined as the selectivity index (SI) and is an indication of the selectivity of the anti-HIV activity of the inhibitor. The ultimate monitoring of HIV-1 infection and cytotoxicity is done using a scanning microscope. Image analysis allows very sensitive detection of viral infection. Measurements are done before cell necrosis, which usually takes place about five days after infection, in particular measurements are performed three days after infection.

Table 2 lists $pEC_{50}$ values against the wild-type HIV-1 IIIB strain as well as pCC50 values for a selected number of compounds of the invention. A $pEC_{50}$ value corresponds to $-\log_{10}(EC_{50})$. A $pCC_{50}$ value corresponds to $-\log_{10}(CC_{50})$.

Listed are compounds having a $pEC_{50}$ value of less than 4.00 to maximum 4.50 $pEC_{50}$. Darunavir, a commercially available HIV protease inhibitor, has an $pEC_{50}$ of 8.17. The $pEC_{50}$ range of <4 to 4.50, when compared to 8.17, is significantly lower in terms of antiviral activity, therefore demonstrating that the compounds of the present invention confer minimal or no resistance to HIV.

Equally, the toxicity values reported for the compounds of the present invention, in a range of less than 4.00 to maximum 4.46 $pCC_{50}$, demonstrate the low or minimal toxicity of these compounds.

TABLE 2 antiviral activity (pEC50) and cytotoxicity
(pCC50) of selected test compounds.

| Compound Nr. | Antiviral Activity IIIB pEC$_{50}$ | Toxicity MT4 pCC$_{50}$ |
|---|---|---|
| C3 | 4.28 | 4.15 |
| C4 | 4.50 | 4.40 |
| C5 | 4.07 | 4.06 |
| C6 | 4.10 | <4.00 |
| C7 | 4.08 | 4.15 |
| C8 | <4.00 | <4.00 |
| C9 | <4.00 | <4.00 |
| C10 | <4.00 | <4.00 |
| C11 | 4.42 | 4.46 |
| C12 | 4.22 | 4.21 |
| C13 | <4.00 | <4.00 |
| C14 | 4.10 | 4.05 |
| C15 | 4.30 | 4.37 |
| C16 | 4.41 | 4.39 |
| C17 | 4.38 | 4.44 |
| C18 | 4.41 | 4.38 |
| C19 | <4.00 | <4.00 |
| C20 | <4.00 | <4.00 |
| C1 | 4.32 | 4.24 |
| C2 | 4.35 | 4.34 |
| C21 | <4.00 | <4.00 |
| C22 | <4.00 | <4.00 |
| C23 | 4.29 | 4.26 |
| C24 | 4.01 | <4.00 |
| C25 | 4.16 | 4.11 |
| C26 | <4.00 | <4.00 |
| C27 | 4.13 | 4.08 |

TABLE 3

Metabolisation of test compound by human liver microsomes after 15 min.

| Compound Nr. | % recovery HLM15 |
|---|---|
| C3 | 54 |
| C4 | 57 |
| C5 | 83 |
| C6 | 81 |
| C7 | 56 |
| C8 | 81 |
| C9 | 55 |
| C10 | 47 |
| C11 | 52 |
| C12 | 67 |
| C13 | 69 |
| C14 | 24 |
| C15 | 57 |
| C16 | 59 |
| C17 | 68 |
| C18 | 57 |
| C19 | 69 |
| C20 | 37 |
| C1 | 56 |
| C2 | 67 |
| C21 | 62 |
| C22 | 77 |
| C23 | 72 |
| C24 | 56 |
| C25 | 63 |
| C26 | 92 |
| C27 | 98 |

Assay 3: Metabolic Stability of Test Compounds (HLM15')

Sub-cellular tissue preparations are made according to Gorrod et al. (Xenobiotica, 5, pp. 453-462 (1975)) by centrifugal separation after mechanical homogenization of tissue. Human liver tissue is rinsed in ice-cold 0.1 M Tris-HCl (pH 7.4) buffer to wash excess blood. Tissue is then blotted dry, weighed and chopped coarsely using surgical scissors. The tissue pieces are homogenized in 3 volumes of ice-cold 0.1 M phosphate buffer (pH 7.4) using either a Potter-S (Braun, Italy) equipped with a Teflon pestle or a Sorvall Omni-Mix homogenizer, for 7×10 sec. In both cases, the vessel is kept in/on ice during the homogenization process. Tissue homogenates are centrifuged at 9000×g for 20 min at 4° C. using a Sorvall centrifuge or Beckman Ultracentrifuge. The resulting supernatant can be stored at −80° C. and is designated 'S9'. The S9 fraction is centrifuged at 100,000×g for 60 min at 4° C. using a Beckman ultracentrifuge. The resulting supernatant is carefully aspirated, aliquoted and designated 'cytosol'. The pellet is re-suspended in 0.1 M phosphate buffer (pH 7.4) in a final volume of 1 ml per 0.5 g original tissue weight and designated 'microsomes'. All sub-cellular fractions are aliquoted, immediately frozen in liquid nitrogen and stored at −80° C. until use.

Test compounds and a NADPH-generating system were added to human liver microsomes ('microsomes' fraction, protein concentration 1 mg/ml) suspended in 0.1 M phosphate buffer (pH=7.4), to get final reaction mixture concentrations of 5 µM test compound, 0.8 mM D-Glucose-6-phosphate, 0.8 mM MgCl$_2$ and 0.8 U/ml of Glucose-6-phosphate dehydrogenase. Heat-inactivated (10 min at 95° C.) 'S9' or microsomes were used for blank experiments. Reaction mixtures were incubated at 37° C. for 5 min, after which the reaction was started by the addition of 0.8 mM β-NADP. The reaction was incubated for 0 or 15 min. Next, the reaction was stopped by addition of 2 volumes of DMSO (or acetonitrile). Samples were centrifuged (10 min, 900×g) and analyzed by LC-MS. Table 3 summarizes the results.

Assay 4: CYP450 Inhibition

Inhibition of the metabolism of test compounds by different CYP P450 isoenzymes was determined using E. coli expressed proteins (3A4, 2C9, 2D6, 1A2, and 2C19) that convert their specific substrates into a fluorescent molecule (Table 6). This fluorescent molecule was measured using a fluorescent plate reader (Victor2 (Wallac) or Fluoroskan (Labsystems)). Compounds inhibiting the enzymatic reaction will result in a decrease of fluorescent signal. CYP P450 enzymes were prepared in house or commercially bought and stored at −80° C. Table 4 summarizes the results.

TABLE 4

Inhibition of CYP450 isoenzymes by test compounds.

| Comp. Nr. | CYP P450 isozymes | | | | | | |
|---|---|---|---|---|---|---|---|
| | 3A4-BFC % inh. | 3A4-BQ % inh. | 3A4-DBF % inh. | 2C9-MFC % inh. | 2D6-AMMC % inh. | 1A2-CEC % inh. | 2C19-CEC % inh. |
| C3 | 95 | 85 | 97 | 99 | 49 | 20 | 90 |
| C4 | 95 | 85 | 99 | 99 | 79 | 62 | 92 |
| C5 | 92 | 82 | 92 | 94 | 41 | 14 | 86 |
| C6 | 82 | 83 | 92 | 96 | 65 | 41 | 94 |
| C7 | 92 | 80 | 94 | 97 | 45 | 13 | 89 |
| C8 | 91 | 79 | 91 | 95 | 39 | 4 | 76 |
| C9 | 91 | 78 | 89 | 85 | 66 | 4 | 64 |
| C10 | 95 | 79 | 93 | 96 | 62 | 33 | 92 |
| C11 | 94 | 78 | 99 | 97 | 86 | 45 | 100 |
| C12 | 70 | 79 | 93 | 92 | 0 | 21 | 81 |
| C13 | 81 | 84 | 94 | 95 | 64 | 8 | 67 |
| C14 | 84 | 80 | 91 | 98 | 67 | 56 | 87 |
| C15 | 75 | 80 | 92 | 97 | 41 | 51 | 92 |
| C16 | 71 | 82 | 92 | 97 | 43 | 50 | 90 |
| C17 | 57 | 81 | 93 | 98 | 46 | 55 | 87 |
| C18 | 83 | 84 | 94 | 98 | 64 | 63 | 93 |
| C19 | 58 | 72 | 92 | 93 | 53 | 43 | 77 |
| C20 | 88 | 66 | 85 | 63 | 13 | 6 | 41 |
| C1 | 77 | 80 | 95 | 97 | 73 | 36 | 94 |

TABLE 4-continued

Inhibition of CYP450 isoenzymes by test compounds.

| Comp. Nr. | 3A4-BFC % inh. | 3A4-BQ % inh. | 3A4-DBF % inh. | 2C9-MFC % inh. | 2D6-AMMC % inh. | 1A2-CEC % inh. | 2C19-CEC % inh. |
|---|---|---|---|---|---|---|---|
| C2 | 100 | 79 | 96 | 96 | 102 | 40 | 98 |
| C21 | 87 | 81 | 95 | 95 | 62 | 43 | 75 |
| C22 | 93 | 74 | 89 | 69 | 62 | 0 | 60 |
| C23 | 94 | 73 | 92 | 89 | 65 | 22 | 77 |
| C24 | 101 | 82 | 89 | 92 | 96 | 13 | 86 |
| C25 | 100 | 79 | 89 | 95 | 91 | 25 | 97 |
| C26 | 95 | 77 | 84 | 82 | 30 | 0 | 35 |
| C27 | 101 | 81 | 90 | 84 | 86 | 10 | 96 |

TABLE 5

Conversions mediated by the respective
E. coli expressed CYP P450 isoenzymes

| Substrate | Enzyme | Fluorescent molecule |
|---|---|---|
| BFC: 7-Benzyloxytrifluoromethyl coumarin | CYP3A4 | 7-HFC: 7-Hydroxytrifluoromethyl coumarin |
| BQ: 7-benzyloxyquinoline | CYP3A4 | 7-HQ: 7-hydroxyquinoline |
| DBF: dibenzylfluorescein | CYP3A4 | fluorescein |
| MFC 7-Methoxy-4-trifluoromethyl coumarin | CYP2C9 | 7-HFC: 7-Hydroxytrifluoromethyl coumarin |
| AMMC: 3-[2-(N,N-diethyl-N-methylamino)ethyl]-7-methoxy-4-methylcoumarin | CYP2D6 | AHMC: 3-[2-(N,N-diethylamino)ethyl]-7-hydroxy-4-methylcoumarin hydrochloride |
| CEC: 7-ethoxy-3-cyanocoumarin | CYP1A2 | CHC: 3-cyano-7-hydroxycoumarin |
| CEC: 7-ethoxy-3-cyanocoumarin | CYP2C19 | CHC: 3-cyano-7-hydroxycoumarin |

The assay was performed in black 96 well Costar plates. Test compounds were added to a CYP P450 enzyme solution in the presence of an NADPH generating system. After 5 min of preincubation at 37° C., the freshly prepared, phosphate buffered (pH 7.4) substrate solution was added. Known CYP P450 inhibitors were used as positive controls, negative controls were run without CYP P450 enzyme. For final reaction mixture concentrations, see Table 6. Reaction mixtures were incubated at 37° C. for 30 min (CYP3A4-BFC), 30 min (CYP3A4-BQ), 10 min (CYP3A4-DBF), 15 min (CYP1A2-CEC), 30 min (CYP2C9-MFC, CYP2C19-CEC), or 45 min (CYP2D6-AMMC), respectively. Then, the reaction was stopped by the addition of 200 μl acetonitrile, and the fluorescent signal was detected.

Calculation of CYP P450 isoenzyme inhibition (% inh.):

% activity=(100/(average positive control−average negative control))×(average sample−average negative control)

% inhibition=100−% activity

Assay 5: % Metabolic Blocking: Inhibition of TMC114 Metabolisation

Darunavir (TMC 114 currently marketed as Prezista™) and tested booster compounds were added to human liver microsomes ('microsomes' fraction, protein concentration 1 mg/ml) suspended in potassium phosphate buffer (pH=7.4), to get final reaction mixture concentrations of 3 μM darunavir and 3 μM test compound. In the non-boosted parallel reactions, test compound was not added.

Boiled human liver microsomes were used for blank experiments. After addition (in a 1:3 (v/v) ratio) of a NADPH generating mixture consisting of β-nicotinamide adenine dinucleotide phosphate (β-NADP, 0.5 mg/ml, 653.2 μM), D-Glucose-6-phosphate (2 mg/ml, 7.1 mM), Glucose-6-phosphate dehydrogenase (1.5 U/ml) in 2% $NaHCO_3$, the reaction mixture was incubated at 37° C. for 30 or 120 minutes after which the reaction was stopped by increasing the temperature to 95° C. Darunavir concentrations were determined using HPLC-MS. The control value, obtained when the percentage TMC114 remaining is determined in the non boosted reaction (=absence of test compound), is 12% (median value of 10 experiments). Table 7 summarizes the results.

TABLE 7

Stability of darunavir in the presence of human
liver microsomes and 3 μM tested booster compound

| Compound Nr. | % Stability of darunavir (% recovery of darunavir after 120') @ 3 μM booster |
|---|---|
| C3 | 82 |
| C4 | 83 |
| C5 | 86 |
| C6 | 87 |
| C7 | 95 |
| C8 | 80 |
| C9 | 25 |
| C10 | NA |
| C11 | 108 |
| C12 | 93 |
| C13 | 72 |
| C14 | 73 |
| C15 | 119 |
| C16 | 86 |
| C17 | 97 |

TABLE 6

Final reaction mixture concentrations for CYP P450 isoenzyme inhibition assay.

| | | CYP3A4-BFC | CYP3A4-BQ | CYP3A4-DBF | CYP2C9-MFC | CYP2D6-AMMC | CYP1A2-CEC | CYP2C19-CEC |
|---|---|---|---|---|---|---|---|---|
| Test compound | | 10 μM | 10 μM | 10 μM | 10 μM | 10 μM | 10 μM | 10 μM |
| NADPH generating system | Glucose-6-Phosphate | 3.3 mM | 3.3 mM | 3.3 mM | 3.3 mM | 0.41 mM | 3.3 mM | 3.3 mM |
| | Glucose-6-Phosphate dehydrogenase | 0.4 U/ml | 0.4 U/ml | 0.4 U/ml | 0.4 U/ml | 0.4 U/ml | 0.4 U/ml | 0.4 U/ml |
| | $MgCl_2$ | 3.3 mM | 3.3 mM | 3.3 mM | 3.3 mM | 0.41 mM | 3.3 mM | 3.3 mM |
| | NADP | 1.3 mM | 1.3 mM | 1.3 mM | 1.3 mM | 8.2 μM | 1.3 mM | 1.3 mM |
| CYP P450 enzyme | | 83 nM | 20 nM | 5 nM | 60 nM | 42 nM | 5 nM | 2.5 nM |
| Substrate | | 150 μM | 60 μM | 1 μM | 200 μM | 3 μM | 5 μM | 25 μM |

TABLE 7-continued

Stability of darunavir in the presence of human liver microsomes and 3 μM tested booster compound

| Compound Nr. | % Stability of darunavir (% recovery of darunavir after 120') @ 3 μM booster |
|---|---|
| C18 | 82 |
| C19 | 103 |
| C20 | 41 |
| C1 | 85 |
| C2 | 100 |
| C21 | 73 |
| C22 | 58 |
| C23 | 89 |
| C24 | 87 |
| C25 | 104 |
| C26 | 39 |
| C27 | 85 |

Booster Influence on Key Pharmacokinetic Parameters of Darunavir

To test the "boosting capacity" (=ability of the compounds to enhance the pharmacokinetics of darunavir) in vivo, representative example compound C12 was given orally (in a suitable vehicle like for example PEG400- or PEG400/30% saline or HpβCD) to a group (n=3) of fed, male Beagle dogs, at a dose of 5 mg/kg body weight, 15 minutes prior to administration of 5 mg/kg body weight darunavir. Oral dosing was done by gavage. At all times, the dogs were given free and continuous access to water. Blood samples were collected from the jugular vein at 0 (=predose), 0.5, 1, 2, 4, 7, and 24 h after dose administration. The samples were centrifuged at 1900×g for 10 min at 5° C. to allow plasma separation. Separated plasma was stored in the freezer within two hours after blood sampling. At all times, blood and plasma samples were placed on melting ice and protected from light. Individual plasma samples were analyzed for darunavir and booster compound by means of LC-MS/MS. Pharmacokinetic parameters for darunavir were calculated using noncompartemental Analysis, WinNonLin software Version 5.0, Pharsight, and are listed in Table 8. Values listed are the average of 3 dogs. Fold change (FC) values indicate the difference with the control experiment in which only 5 mg/kg darunavir was given.

TABLE 8

Booster influence on key pharmacokinetic parameters of darunavir.

| Compound Nr. | AUC ng · h/mL | $C_{max}$ ng/mL | $C_{7h}$ ng/mL | FC AUC | FC $C_{max}$ | FC $C_{7h}$ |
|---|---|---|---|---|---|---|
| C12 | 1574 | 892 | 24 | 3 | 2 | 8 |

Experimental

Reagents were purchased from commercial sources and were used as received. Thin layer chromatography was performed on silica gel 60 $F_{254}$ plates (Merck). LC-MS analysis was done using either one of the following methods. Data for compounds C1-27 are listed in Table 1 (see above)

LCMS-Method 1

HPLC-system: Waters Alliance 2695 (pump+auto sampler), Waters 996 (Photo diode array-Detector)

Column: Waters XTerra MS C18 2.5 μm 50×4.6 mm
Temperature: 55° C.
Mobile phase: A: 10 mM $HCOONH_4$+0.1% HCOOH in $H_2O$
B: $CH_3CN$ Gradient: 0min: 15% B, 3 min: 95% B, 4.2 min: 95% B
Equilibration time: 1.2 min
Flow: 2 ml/min
Injection volume: 5 μl of a 0.5 mg/ml solution
MS-detector: Waters ZQ
Ionisation: electrospray in positive and negative mode LCMS-Method 2

HPLC-system: Waters Alliance 2790 (pump+autosampler), Waters 996 (Photo diode array-detector)

Column: Waters SunFire C18 3.5 μm 100×4.6 mm
Temperature: 55° C.
Mobile phase: A: 10 mM $NH_4OOCH$+0.1% HCOOH in $H_2O$
B: acetonitril
Gradiënt: 0 min: 5% B, 5.4 min: 95% B, 7.2 min: 95% B
Equilibration time: 1.8 min
Flow: 1.5 ml/min
Injection volume: 5 μl of a 0.5 mg/ml solution
MS-detector: Waters LCT
Ionisation: electrospray in positive and negative mode NMR spectra were recorded on a Bruker Avance 400 spectrometer, operating at 400 MHz. Chemical shifts are given in ppm and J values in Hz. Multiplicity is indicated using the following abbreviations: d for doublet, t for a triplet, m for a multiplet, etc. Compound names were generated using Chemdraw Ultra, version 9.0.7 (CambridgeSoft).

Chemistry

The compounds of formula (I) were prepared according the general method provided below exemplified by the detailed procedures described for the synthesis of C12.

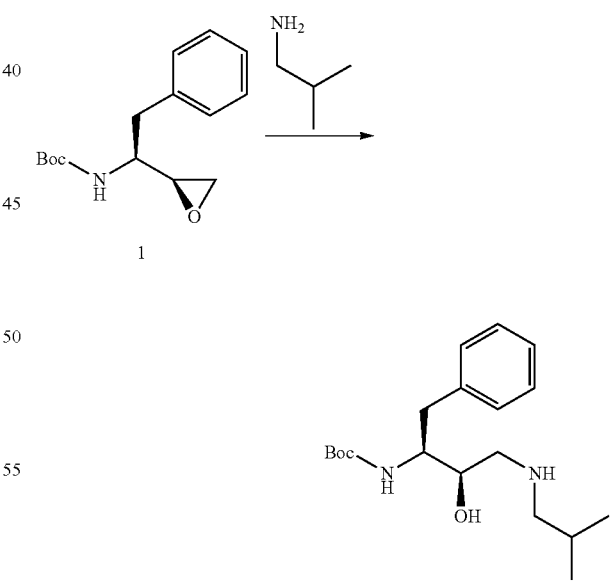

A solution of 1 (1.0 eq., 106 mmol, 28.0 g) and isobutylamine (1060 mmol, 10 eq., 106 mL) in isopropanol (200 mL) was stirred at 80° C. for 3 h. The solvent was evaporated under reduced pressure and the crude product 2 was used as such in the next step.

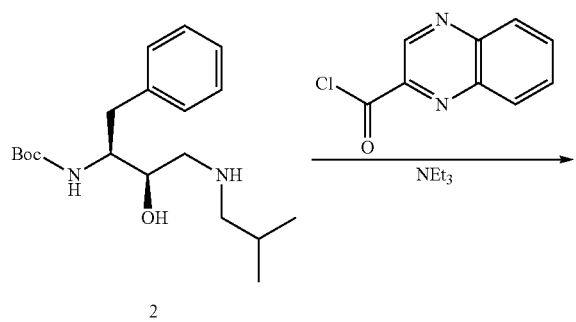

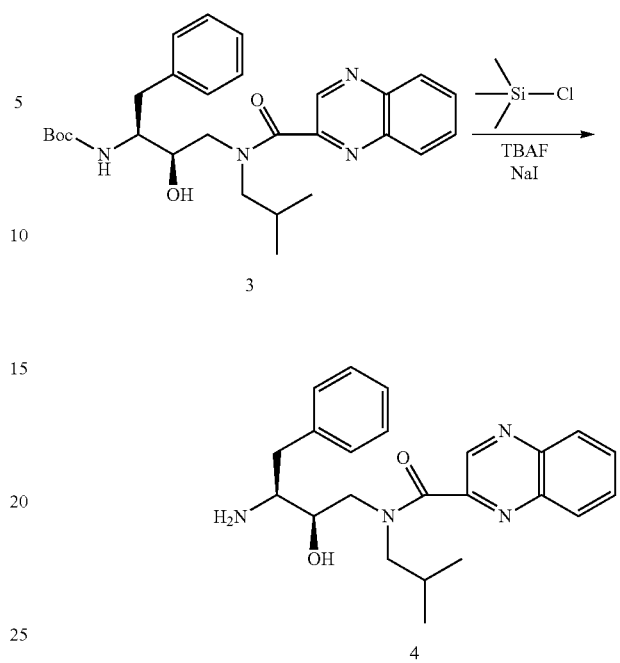

A solution of 2 (32.53 g, 97 mmol, 1.0 eq.), quinoxaline-2-carbonyl chloride (18.62 g, 97 mmol, 1.0 eq.) and triethylamine (40.4 mL, 291 mmol, 3.0 eq.) in THF (200 mL) was stirred at room temperature for 2 h. Water was added and extraction was carried out with CH$_2$Cl$_2$. The combined organic phases were washed twice with saturated aqueous NaHCO$_3$ solution, dried with MgSO$_4$ and concentrated in vacuo. The residue was purified by column chromatography on silica gel (0-3% MeOH in CH$_2$Cl$_2$) to give 3 (46.69 g, yield=98%).

A solution of 3 (19.58 g, 40 mmol, 1.0 eq.), chloro-trimethyl-silane (12.95 g, 120 mmol, 3.0 eq.), sodium iodide (23.83 g, 160 mmol, 4.0 eq.) and TBAF (199 mL, 200 mmol, 5.0 eq., 1.0 M solution in THF) in acetonitrile (150 mL) was stirred at RT for 1 h. Water was added and extraction was carried out with CH$_2$Cl$_2$. The combined organic phases were dried with MgSO$_4$ and concentrated in vacuo. The crude product was used as such in the next step.

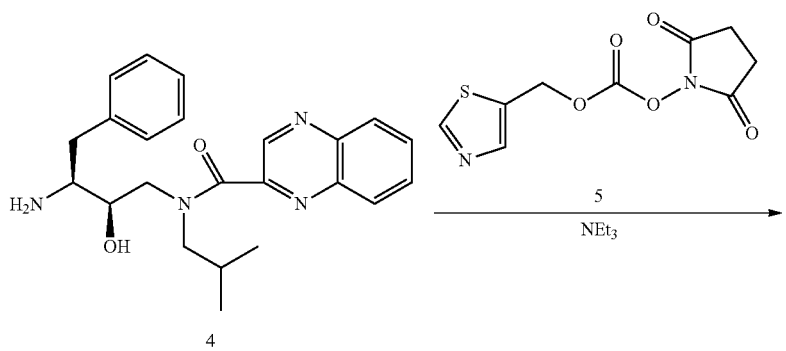

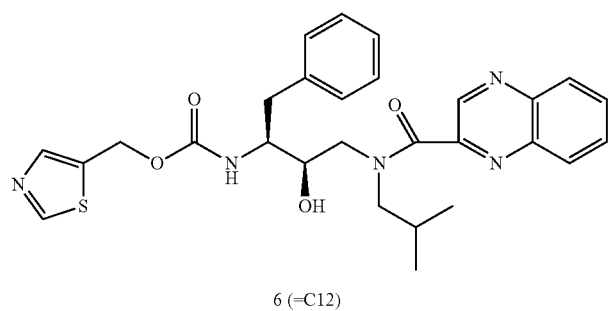

A solution of 4 (36.0 g, 92 mmol, 1.0 eq.), 5 (32.4 g, 127 mmol, 1.38 eq.) and triethylamine (18.28 mL, 131 mmol, 1.43 eq.) in acetonitrile (500 mL) was stirred at room temperature for 2 h. Water was added and extraction was carried out with $CH_2Cl_2$. The combined organic phases were washed twice with saturated aqueous $NaHCO_3$ solution, dried with $MgSO_4$ and concentrated in vacuo. The residue was purified by column chromatography on silica gel (0-2% $NH_3$ (7M solution in MeOH) in $CH_2Cl_2$) to give 6. A second purification by column chromatography on silica gel (EtOAc) was necessary to remove residual TBAF and to give pure 6 (=C12) (38.2 g, yield=78%, purity (LC)=94%). The NMR spectrum showed presence of two rotamers present in a 2-1 ratio. $^1$H-NMR ($CDCl_3$), major rotamer: 9.28 ppm (s, 1H), 8.78 (s, 1H), 8.21 ppm (dd, 1H, J=8.41, J=2.2), 8.09 (m, 1H), 7.92-7.8 (m, 2H); 7.77 (s, 1H); 7.3-7.05 (m, 5H); 6.6 (d, 1H, J=6.49); 5.24 (d, 1H); 5.14 (s, 2H); 4.93 (d, 1H, J=9.32); 4.0 (m, 2H); 3.8 (m, 2H); 3.67 (m, 1H); 3.51 (d, 1H, J=7.46), 3.3-3.2 (m, 2H); 3.0-2.84 (m; 2H); 2.18 (sep, 1H, J=7.46), 1.0 (m, 6H)

The invention claimed is:
1. A compound having the formula (II)

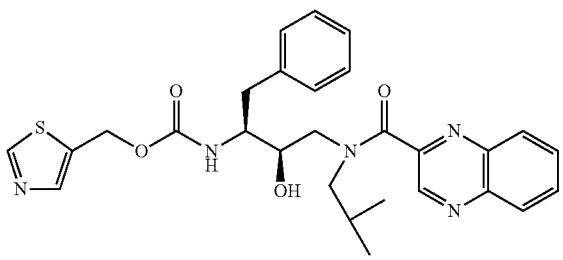

(II)

or pharmaceutically acceptable salts and stereoisomers thereof.

* * * * *